US006503533B1

(12) United States Patent
Korba et al.

(10) Patent No.: US 6,503,533 B1
(45) Date of Patent: Jan. 7, 2003

(54) ANTISENSE OGLIGONUCLEOTIDES AGAINST HEPATITIS B VIRAL REPLICATION

(75) Inventors: Brent E. Korba, Laurel; John L. Gerin, Bethesda, both of MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/199,269

(22) Filed: Nov. 25, 1998

Related U.S. Application Data

(60) Continuation of application No. 08/888,695, filed on Jul. 7, 1997, now abandoned, which is a division of application No. 08/281,106, filed on Jul. 28, 1994, now Pat. No. 5,646,262.

(51) Int. Cl.[7] ...................... A61K 31/711; A61K 9/127; C07H 21/04; C12N 15/11

(52) U.S. Cl. .................. 424/450; 514/44; 536/23.1; 536/24.5; 435/455; 435/458; 435/325; 435/370

(58) Field of Search ..................... 424/450; 514/44; 536/23.1, 24.5; 435/455, 458, 325, 370

(56) References Cited

U.S. PATENT DOCUMENTS

| 5,627,158 A | 5/1997 | Cho-Chung |
| 5,744,460 A | 4/1998 | Muller et al. |
| 5,767,102 A | 6/1998 | Draper et al. |
| 5,886,000 A | 3/1999 | Shoji et al. |
| 6,040,296 A | 3/2000 | Nyce |
| 6,087,343 A | 7/2000 | Phillips et al. |
| 6,096,722 A | 8/2000 | Bennett et al. |

FOREIGN PATENT DOCUMENTS

| WO | WO 95/19433 A2 | 7/1995 |
| WO | WO 96/03152 | 2/1996 |
| WO | 96/39502 | 12/1996 |
| WO | 97/03211 | 1/1997 |

OTHER PUBLICATIONS

KarenPihl–Carey et al, BIO WORLD TODAY, The Daily Biotechnology Newspaper, Isis To Restructure As Crohn's Disease Drug Fails in Phase 111, vol. 10, No. 239 p. 1 of 5 Dec. 16, 1999.*
Robert W. Wallace, Does antisense make sense?. DDt vol. 4, No. 1 Jan. 1999.*
Korba et al., Antiviral Res, vol. 19, pp. 55–70, 1992.*
Korba et al., Antiviral Res., vol. 15, pp. 217–222, 1991.*
Putlitz et al., Gastroenterology, vol. 115, pp. 702–713, 1998.*
Gura, T., Science, vol. 270, pp. 575–577, Oct. 27, 1995.*
Nature Biotechnology, vol. 15, pp. 519–528, Jun. 1997.*
Branch, A.D., TiBS, vol. 23, pp. 45–50, Feb. 1998.*
Hepatitis Weekly, Publisher: Charles W. Henderson, Dec. 15, 1997.*

U.S. application No. 08/181,557, Carmichael et al, filed Jan. 12, 1994.
U.S. application No. 08/287,337, Camichael et al, filed Aug. 8, 1994.
"Hepatitis B virus", International Antiviral News, vol. 2, 1994, p. 59, XP002085113, lines 3–22, & 7th International Conference on Antiviral research, Charleston S.C., USA, Feb. 27, 1994–Mar. 3, 1994.
Korba et al.: Inhibition of hepatitis B virus replication in vitro by antisense oligonucleotides: ANTIVIRAL RES.; (1994) 23, Suppl. 1,78, XP002085114, Abstract 80.
Hirsch et al: "CIS–Acting Sequences Required for Encapsidation of Duck Hepatitis B Virus Pregenomic RNA", Journal of Virology, vol. 65, No. 6, Jun. 1991, pp 3309–3316, XP000614651.
Korba et al.: "Antisense Oligonucleotides are effective inhibitors of hepatitis B v irus replication in vitro", antiviral research, vol. 28, 1995, pp 225–242, XP00063334.
Agrawal, S., et al. "Pharmacokinetics of Antisense Oligonucleotides,"*Clin. Pharmacokinet*, 28:7–1 (1995).
Bartholomew, R. M., et al. "Targeted Delivery Of Antisense DNA In Woodchuck Hepatitis Virus–Infected Woodchucks, "*J. Viral Heptitis*, 2:273–278 (1995).
Bassendine, M.F., et al. "Adenine Arabinoside Therapy in HBeAg–Positive Chronic Liver Disease: A Controlled Study,"*Gastroenterol*, 80:1016–1020 (1981).
Bayever, E., et al. "Systemic Administration of a Phosphorthioate Oligonucleotide with a Sequence Complementary to p53 for Acute Myelogenous Leukemia and Myelodysplastic Syndrome: Initial Results of a Phase I Trial,"*Antisense Res. Dev.*, 3:383–90 (1993).
Cunningham, C. Casey, et al. "A Phase I Trial of c–Raf Kinase Antisense Olignucleotide ISIS 5132 Administered as a Continuous Intravenous Infusion in Patients with Advanced Cancer," *Clin, Cancer Res.*, 6:1626–31 (May 2000).
Dean, Nicolas M., et al. "Inhibition of Protein Kinase C–α Expression in Human A549 Cells by Antisense Oligonucleotides Inhibits Induction of Intercellular Adhesion Molecule 1 (ICAM–1) mRNA by Phorbol Ester," *J. Biol. Chem.*, 269:16416–16424 (Jun. 1994).
Diapola, Robert S., et al., "Evidence For A Functional Kit Receptor In Melanoma, Breast, And Lung Carcinoma Cells," *Cancer Gene Therapy*4(3):176–182 (1997).
Field, A.K. "Viral Targets For Antisense Oligonucleotides: A Mini Review," *Antiviral Res.*, 37:67–81 (1998).

(List continued on next page.)

*Primary Examiner*—David Guzo
(74) *Attorney, Agent, or Firm*—King & Spalding; Sherry M. Knowles; Joseph M. Bennett-Paris

(57) ABSTRACT

Antisense oligonucleotides that hybridize to segments of the pres1, S, C, and ε regions of the hepatitis B virus (HBV) RNA pregenome inhibit replication of the virus. Pharmaceutical compositions which contain these oligonucleotides as the active ingredients are effective against HBV infection.

16 Claims, 6 Drawing Sheets

OTHER PUBLICATIONS

Fourel, I., et al. "Effects of 2'–Fluorinated Arabinosyl–Pyrimidine Nucleosides on Duch Hepatitis B Virus DNA Level in Serum and Liver of Chronically Infected Ducks,"*J. Med Virol.*, 37:122–126 (1992).

Fried, Michael W., et al. "Therapy of Chronic Hepatitis B with a 6–Month Course of Ribavirin," *J. Hepatol.*, 21:145–150 (1994).

Galderisi, Umnerto, et al. "Antisense Oligonucleotides as Therapeutic Agents," *J. Cell. Physiol.*, 181:251–257 (1999).

Gangemi, J. David, et al. "Antiviral and Anti–Proliferative Activities of ∀Interferons in Experimental Hepatitis B Virus Infections,"*Antiviral Therapy*, 1:64–70 (1997).

Gerin, John L., et al. "A Preliminary Report of A Controlled Study of Thymosin Alpha–1 in the Woodchuck Model of Hepadnavirus Infection," in *Advances in Antiviral Drug Development and Detection of Virus Infections*, New York: Plenum Press, (1992) pp. 121–123.

Hadziyannis, S., et al. "Interferon Treatment With or Without Oral Granciclovir in HBeAg–Negative Chronic Hepatitis B: A Randomized Study," *J. Viral Hepatol.*, 7:235–240 (2000).

Jaeckel, Elmar, and Michael P. Manns. "Experience With Lamivudine Against Hepatis B Virus," *Intervirology*, 40:322–336 (1997).

Janssen, Harry L.A., et al. "Interferon–α and Zidovudine Combination Therapy for Chronic Hepatitis B: Results of a Randomized, Placebo–Controlled Trial," *Hepatol*, 17:383–288 (1993).

Korba, Brent E. and Malcolm R. Boyd. "Penciclovir Is a Selective Inhibitor of Hepatitis B Virus replication in Cultured Human Hepatoblastoma Cells" *Antimicrobial Agents & Chemotherapy*, 40:1282–1284 (1996).

Korba, Brent E., et al. "Enhanced Antiviral Benefit of Combination Therapy With Lamivudine and Famciclovir Aganist WHV Replication in Chronic WHV Carrier Woodchucks," *Antiviral Research*, 45:19–32 (2000).

Korba, Brent E., et al. "Enhanced Antiviral Benefit of Combination Therapy With Lamivudine andd Alpha Interferon Against WHV Replication in Chronic Carrier Woodchucks," *Antiviral Therap.*, 5:95–104 (2000).

Korba,, Brent E., et al. "Treatment of Chronic Woodchuck Hepatitis Virus Infection in the Eastern Woodchuck (*Marmota Monax*) With Nucleoside Analogues Is Predictive of Therapy for Chronic Hepatitis B Virus Infection in Human, " *Hepatol.*, 31:1165–1175 (2000).

Korba, Brent E. "In Vitro Evaluation of Combination Therapies Against Hepatitis B Virus Replication," *Antiviral Research*, 29:49–51 (1996).

Krieg Arthur M. "Mechanisms And Application Of Immune Stimulatory CpG Oligodeoxynucleotides," *Biochimica et Biophysisca Acta*, 1489:107–16 (1999).

Lau, George K.,et al., "Combination Therapy With Lamivudine and Famciclovir for Chronic Hepatitis B–Infected chinese Patients: A Viral Dynamics Study," *Hepatol.*, 32:394–399 (2000).

Luscombe, Carolyn, et al. "Long Term Ganciclovir Chemotherapy for Congenital Duck Hepatits B Vius Infection In Vivo: Effect on Intraheptic–Viral DNA, RNA, and Protein Expression," *Hepatol.*, 24:766–773 (1996).

Marcussan, E. G., et al. "Preclinical and Clinical Pharmacology of Antisense Oligonucleotides," *Molecular Biotechnology*, 12:1–11 (1999).

McKenzie, Robin, et al. "Hepatic Failure and Lacttic Acidosis Due to Fialuridine (FIAU), an Investigational Nucleoside Analogue for Chronic Hepatitis B," *New England J. of Medicine*, 333:1099–1105 (1995).

Moriya, K., et al. "In Vivo Inhibition of Hepatitis B Virus Gene Expression by Antisense Phosphorothioate Oligonucleotides," *Biochem. Biophys. Res. Comm.*, 218:217–233 (Jan. 1996).

Mutimer, David, et al. "Combination Alpha–Interferon and Lamivudine Therapy for Alpha–Interferon–Resistant Chronic Hepatitis B Infection: Results of a Pilot Study," *J. Hepatol.*, 28:923–932 (1998).

Nicoll, A.J., et al. "Inhibition of Duck Hepatitis B Virus Replication by 9–(2–Phosphonylmethoxyethyl)adenine, An Acryclic Phosphonate Nucleoside Analogue," *Antimicrobial Agents & Chemotherapy*, 42:3130–3135 (1998).

Offensperger, W. B., et al. "Antisense Therapy of Hepatitis B Virus Infection," *Mol. Biotechnol.*, 9:161–170 (1998).

Offensperger, W.B., et al. "In Vivo Inhibition of Duck Hepatitis B Virus Replication and Gene Expression By Phosphorothioate Modified Antisense Oligodeoxynucleotides," *EMBO J.*, 12(3):1257–1262 (1993).

Omata, Masao, et al. "In Vivo Study of the Mechanism of Aciton of Antiviral Agents Against Hepadna Virus Replication in the Liver," *J. Hepatol.*, 3:S49–S55 (1986).

Perillo, Robert, et al. "Adefovir Dipivoxil for the Treatment of Lamivudine–Resistant Hepatitis B Mutants," *Hepatol.*, 32:129–134 (2000).

Reed, John C., et al. "Antisense–Mediated Inhibition of *BCL2* Protooncogene Expression and Leukemic Cell Growth and Survival: Comparisons of Phosphodiester and Phosphorothioate Oligodeoxynucleotides," *Cancer Research*, 50:6565 (Oct. 15, 1990).

Schinazi, Raymond F., et al. "Cell–Based and Animal Models for Hepatitis B and C Viruses," *Antiviral Chemistry and Chemotherapy*, 10:99–114 (1999).

Schlam, S.W., et al., "Acyclovir, Oral, Intravenous and Combined with Interferon for Chronic HbeAg–Positive Hepatitis," *J. Hepatol.*, 3(suppl 2):S137–141 (1986).

Seifer, Maria, et al. "In Vitro Inhibition of Hepadnavirous Polymerases by the Triphosphates of BMS–200475 and Lobucavir," *Antimicrobial Agents & Chemotherapy*, 42:3200–3208 (1998).

Soni, Paresh N., et al. "Biodistribution, Stability, and Antiviral Efficacy of Liposome–Entrapped Phosophorothioate Antisense Oligodeoxynucleotides in Ducks for the Treatment of Chronic Duck Hepatitis B Virus Infection," *Hepatol.*, 28:1402–1410 (1998).

Tencza , Michael G. and John E. Newbold. "Heterogeneous Response for a Mammalian Hepadnavirus Infection to Accyclovir: Drug–Arrested Intermediates of Minus–Strand Viral DNA Synthesis Are Enveloped and Secreted From Infected Cells as Virion–Like Particles," *J. Med Virol.*, 51:6–16 (1997).

Tennant, Bud C., et al. "Anntiviral Activity and Toxicity of Fialuridine in the Woodchuck Model of Hepatits B Virus Infection," *Hepatol.*, 28:179–191 (1998).

Tomita, T., et al. "Decrease of Wild–Type and Precore Mutant Duck Hepatitis B Virus Replication During Lamivudine Treatment in White Pekin Ducks Infected With The Viruses," *J. Hepatol.*, 32:850–858 (2000).

Trepo, Christian, et al. "Famciclovir in Chronic Hepatitis B: Results of a Dose–Finding Study," *J. Hepatol.*, 32:1011–1018 (2000).

Tsiquaye, K.N., et al. "Antiviral Activity of the Polybasic Anion, Suramin and Acyclovir in Hepadna Virus Infection," *J. Antimicrob. Chemother.*, 18(suppl B) 223–228 (1986).

Tsiquaye, K.N., et al. "Oral Famciclovir Against Duck Hepatitis B Virus Replication in Hepatic and Nonhepatic Tissues of Ducklings Infected in Ovo," *J. Med. Virol.*, 42:306–310 (1994).

Waters, Justin S., et al. "Phase I Clinical and Pharmacokinetic Study of Bcl–2–Antisense Oligonucleotide Therapy in Patients with Non–hodgkin's Lymphoma," *J. Clin. Oncol.*, 18(9):1812–1823 (May 2000).

Wu, George Y., et al., "Specific Inhibition of Hepatitis B Viral Gene Expression in Vitro by Targeted Antisense Oligonucleotides," *J. Biol. Chem.*, 267:12436–12439 (1992).

Xin, Wei and Jui H. Wang. "Treatment of Duck Hepatitis B Virus by Antisense Poly–2'–O0(2,4–Dinitrophenyl)–Oligoribonucleotides," *Antisense Nucleic Acid Drug Dev.*, 8:459–468 (1998).

Yao, Z.Q., et al. "Inhibition of Hepatis B Virus In Vitro by Antisense Oligonucleotides," *Acta Virol.*, 40:35–39 (1996).

Zahm, F.E, et al. "Antiviral Activity of Ganciclovir, 9–(1, 3–dihydroxymethyl) Guanline Against Woodchuck Hepatitis Virus: Quantitative Measurement of Woodchuck Hepatitis Virus DNA Using Storage Phosphor Technology," *Italian J. Gastroenterol. Hepatol.*, 30:510–516 (1998).

Zavaglia, Claugio, et al. "Antiviral Therapy of HBA–and HCV–Induced Liver Cirrhosis," *J. Clin. Gastroenterol.*, 30:234–241 (2000).

Zhang, Hong, et al. "Reduction of Liver Fas Expression By An Antisense Oligonucleotide Protects Mice From Fulminant Hepatitis," *Nature Biotechnology*, 18:862–867 (2000).

Zhiqiang, Y., et al. "In Vivo Inhibition of Hepatitis B Viral Gene Expression By Antisense Phosphorothioate Oligodeoxynucleotides In Athymic Nude Mice," *J. Viral Hepatitis*, 3:19–22 (1996).

Zu Putlitz, Jasper and Jack R. Wands. "Specific Inhibition of Hepatitis B Virus Replication by Sense RNA," *Antisense & Nucleic Acid Drug Dev.*, 9:241–252 (1999).

Zu Putlitz, Jasper, et al. "Antisense RNA Complementary to Hepatitis B Virus Specifically Inhibits Viral Replication," *Gastroenterology*,115:702–713 (1998).

* cited by examiner

ANTISENSE OGLIGONUCLEOTIDES AGAINST HEPATITIS B VIRAL REPLICATION

This application is a continuation of application Ser. No. 08/888,695, filed Jul. 7, 1997, abandoned, which is a divisional of application Ser. No. 08/281,106, filed Jul. 28, 1994, now U.S. Pat. No. 5,646,262.

BACKGROUND OF THE INVENTION

The present invention was made utilizing funds from contracts NO1-AI-72623 and NO1-AI-45179 between the National Institute for Allergy and Infectious Diseases and Georgetown University.

The present invention relates to compositions for the treatment of Hepatitis B virus (HBV) infection. In particular, the invention relates to antisense oligonucleotides and their use to inhibit HBV replication.

Hepatitis B virus, a member of the Hepadnaviridae family, is a blood-borne, hepatotropic pathogen which infects large numbers of people annually. In 1987 there were approximately 25,000 newly reported cases of disease attributable to HBV infection in the US. It is estimated that 60–70% of HBV infections lead to subclinical (asymptomatic) disease, and it is therefore probable that the actual number of new HBV infections each year is much higher. Of those infected with HBV, 90% make a full recovery, but 2–10% of infected patients develop chronic, persistent HBV infection. It is estimated that 1 million people in the US and 300 million people worldwide are chronically infected with HBV. In parts of Asia and Africa it is thought that between 5 and 20% of the population are chronically infected with HBV.

There is strong evidence linking chronic HBV infection to the incidence of primary hepatocellular carcinoma (HCC). Epidemiological studies demonstrate a much higher rate of HCC in regions of the world where HBV infection is endemic than in regions where infection is relatively low. A study in Taiwan demonstrated that HBV carriers (those chronically infected with the virus) were over two hundred times more likely to develop HCC as non-carriers. At the molecular level HBV DNA integration into the host genome has been demonstrated in nearly all hepatocellular carcinomas where HBV infection was present. This integration closely resembles that undergone by other tumor-causing viruses prior to malignant transformation. Over 500,000 deaths per year worldwide have been attributed to HCC, and hence a means of reducing the incidence of this cancer caused by HBV would be highly desirable.

Prior art has demonstrated that the course and outcome of HBV infections relates largely to the interaction of the duration and level of HBV replication and the degree of the host immune response. The severity of HBV-induced disease is, therefore, directly linked to HBV replication. See, for example, Purcell et al. "Hepatitis Viruses" In: DIAGNOSTIC PROCEDURES FOR VIRAL, RICKETTSIAL AND CHLAMYDIAL INFECTIONS. N. Schmidt et al., Ed. 6th Edition, pp 957–1065 (1989).

The only treatment for HBV currently licensed in the United States is alpha interferon. However this drug is not an effective treatment for all HBV chronic carriers and produces substantial side effects in some individuals during prolonged treatment. See, for example, Hoofnagle, "Current Status and Future Directions in the Treatment of Chronic Viral Hepatitis" In: VIRAL HEPATITIS AND LIVER DISEASE, Hollinger F. B. et al. (Eds.), pages 632–3. The majority of new approaches to the development of new antiviral agents against HBV have focused on the use of nucleoside analogues to inhibit the activity of viral polymerases. See Hoofnagle, supra. The limited success of this strategy against other viruses, together with the appearance of drug-resistant viral strains, indicates that this approach is unlikely to be a panacea.

A more recent approach to treatment of chronic HBV infection is the use of antisense oligonucleotides to inhibit viral gene expression. Goodarzi et al., *J. Gen. Virol.* 71: 3021 (1990); Wu et al., *J. Biol. Chem.* 267: 12436 (1992). The use of antisense oligonucleotides is known in the art. For a review, see Stein et al., *Cancer Research* 48: 2659 (1988). The method presents many technical hurdles however, and requires extensive experimentation if a successful outcome is to be achieved. See Stein and Chang, *Science* 261: 1004 (1993). Use of the antisense method to inhibit replication of HBV requires knowledge of both the sequence of the HBV genome (to design suitable complementary oligonucleotides) and of the viral replication cycle (to target those regions of the genome critical to replication). Both the structure of the hepatitis B virus particle, known as a virion, and the viral replication cycle are well understood. See, for example, Tiollais et al., *Nature* 317: 489 (1985), Wang and Seeger, *J. Virol.* 67: 6507 (1993).

Goodarzi et al. prepared six antisense oligonucleotides against the S gene region of the HBV RNA pregenome, and measured their effects on HBsAg production in PLC/PRF/5 cells, which carry an unknown number of chromosomally integrated copies of HBV. Five of the six oligonucleotides proved effective at inhibiting production of HBsAg by the cells. The cell line used was not an ideal model for HBV replication in vivo however, since the HBV in this cell line is integrated as fragmented and rearranged pieces which cannot support HBV replication. Effects on HBV DNA and RNA were not measured.

Wu et al. described the use of a single antisense oligonucleotide targeted at the HBV polyadenylation signal/sequence, linked to a carrier intended to bind specifically to asialoglycoprotein receptors, which are abundant in the liver. The complex showed inhibition of HBsAg production, but the uncomplexed oligonucleotide was much less active. Again, effects on HBV DNA and RNA were not measured.

It is apparent therefore that new treatments for chronic HBV infection are greatly to be desired. In particular, it is greatly desirable to provide compositions and methods for treatment which are highly effective, but have a much lower incidence of side effects than those currently available.

SUMMARY OF THE INVENTION

It is therefore an object of this invention to provide compositions which provide a therapy for chronic hepatitis B virus infection by providing compositions that inhibit the replication of hepatitis B virus.

It is a further object of this invention to provide antisense oligonucleotides which inhibit hepatitis B virus replication by controlling at least one of the steps of virus transcription, translation, encapsidation, and virus release from a host cell.

It is a further object of this invention to provide antisense oligonucleotides which inhibit hepatitis B virus replication by controlling the synthesis of at least one member of the hepatitis B antigen group consisting of HBsAg, HBcAg, HBeAg, pres1 and Pol.

In accomplishing the foregoing objects of the invention, there has been provided, in accordance with one aspect of the current invention, a composition containing at least one antisense oligonucleotide capable of hybridizing specifically to segments of HBV RNA controlling the synthesis of at least one member of the hepatitis B antigen group consisting of HBsAg, HBcAg, HBeAg, pres1 and Pol.

In accordance with another aspect of the current invention, a composition has been provided that contains at least one antisense oligonucleotide capable of hybridizing specifically to HBV messenger RNA encoding regions of at least one HBV gene selected from the group of pres1, S, C, e, pol, and the e encapsidation signal sequence.

There has been provided, in accordance with yet another aspect of the current invention, pharmaceutical compositions comprising an effective amount of at least one of the antisense oligonucleotides of the invention in combination with a pharmaceutically acceptable, sterile vehicle.

In accordance with yet another aspect of the current invention a method has been provided for treating chronic HBV infections in a patient by administering to the patient at least one antisense oligonucleotide which inhibits HBV replication.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Figure 1:
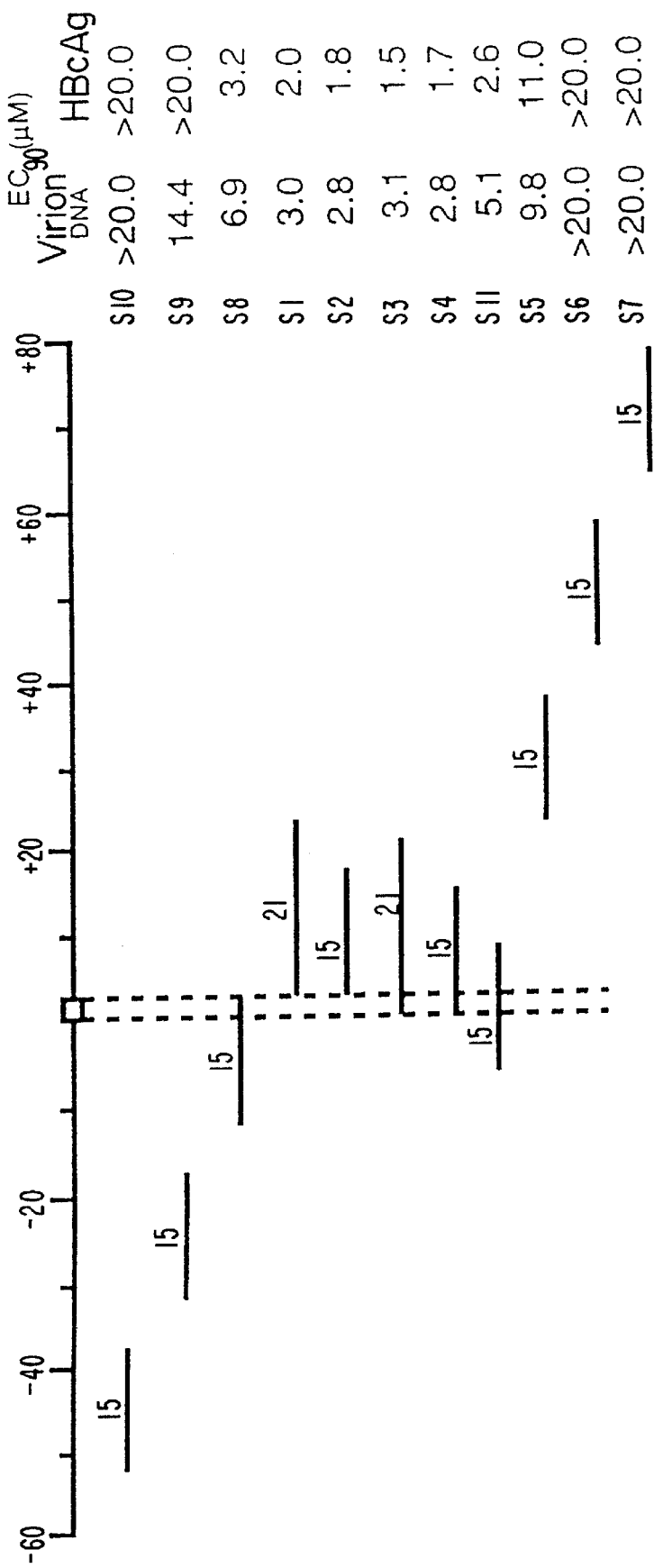
FIG. 1 shows the effect of antisense oligonucleotides targeting the S gene on HBV virion production. The open box denotes the AUG start codon of the S gene. Coordinates are nucleotides relative to the "A" (nucleotide "+1") of the AUG start codon. Lines indicate the relative position of the different oligonucleotides; numbers above each line indicate the length (in nucleotides) of each molecule.

The present invention provides a means of inhibiting the replication of hepatitis B virus (HBV), thus providing a therapy for treating chronic HBV infection. The invention is based on the use of antisense oligonucleotides which anneal to HBV-specific single-stranded RNA, and which thereby inhibit production of proteins essential to HBV replication. Inhibition of viral replication leads to alleviation of disease caused by the virus.

In accordance with the present invention oligonucleotides are provided that are designed to be complementary to portions of the mRNA coding for essential HBV proteins, or to regions of viral RNA which act as signal sequences, and thereby to disrupt the functions of these RNA's.

The present invention also includes pharmaceutical compositions comprising an effective amount of at least one of the antisense oligonucleotides of the invention in combination with a pharmaceutically acceptable sterile vehicle, as described in REMINGTON'S PHARMACEUTICAL SCIENCES: DRUG RECEPTORS AND RECEPTOR THEORY, (18th ed.), Mack Publishing Co., Easton Pa. (1990).

The HBV virion consists of a viral envelope together with a nucleocapsid made up of the virus genome, a multifunctional polymerase, and a core protein. The viral envelope contains three viral surface antigens (HBsAg, preS1, preS2) surrounding a nucleocapsid comprised of core antigen (HBcAg). An additional protein, the soluble e antigen (HBeAg) is observed in the serum of patients with active HBV infection, though its function is as yet unknown.

The virus genome consists of a relaxed circular, partially double-stranded DNA molecule held together by hydrogen bonding of the 5' cohesive termini. The minus strand has an invariable length of approximately 3.2 kb, whereas the plus strand is of variable length, ranging from 50 to 100% of the minus strand. The genome is organized into four partially overlapping open reading frames: the preC/C gene encoding the core and e proteins, the POL gene encoding the multifunctional polymerase (reverse transcriptase, DNA polymerase, Rnase H, terminal DNA binding protein), the preS/S gene encoding the envelope proteins, and the X gene encoding the transcriptional transactivator protein.

After infection, virion DNA is converted to a closed circular form, which then acts as a template for the synthesis of an RNA transcript known as the pregenome. The RNA transcript serves as a template for synthesis of minus strand DNA, which in turn is a template for synthesis of plus strand DNA. This double stranded DNA is then circularized, and the plus strand DNA is further extended to form the open circular form found in mature virus particles. It is essential for viral replication that the reverse transcription, RNase H, and DNA polymerase steps occur inside the nucleocapsid. It is known that a short, approximately 85bp sequence upstream of the preC gene, known as the ε sequence acts as a signal sequence for encapsidation when the viral core and polymerase proteins are present. See, for example, Pollack et al., *J. Virol.* 67: 3254 (1993). Disruption of ε by site-specific mutational analysis is known to inhibit packaging of HBV pregenomic RNA, an essential step in HBV replication. The replication pathway of hepadnaviruses produces intracellular viral DNA that, when examined by gel electrophoresis and blot hybridization techniques, presents as a heterogeneous smear (approximately 0.5 to 3.2 kb) comprised of single-stranded and partially double-stranded linear and circular viral DNA molecules. These are collectively referred to as viral DNA replication intermediates [RI]. See, for example, Fowler et al., *J. Med. Virol.* 13: 83 (1991). The levels of extracellular hepadnaviral virion DNA and intracellular RI are the most reliable parameters used to measure the current level of hepadnaviral replication. Accordingly, these parameters are those most commonly used to determine the effectiveness of antiviral therapy in man, experimental animal models and cell culture. See, for example, Hoofnagle, supra, Korba et al., Woodchuck Hepatitis Virus Infection As A Model For The Development Of Antiviral Therapies Against HBV In: VIRAL HEPATITIS AND LIVER DISEASE, Lemmon et al., Eds. p. 663 (1991), Korba et al., *Antiviral Res.* 15: 217 (1991).

A. Measurement of the Antiviral Effects of Antisense Oligonucleotides

In accordance with the present invention, an in vitro assay system is used which allows the accurate measurement of the antiviral effects of antisense oligonucleotides. In a preferred embodiment of the invention the assay uses a cell line of human origin which allows the replication of HBV in a manner similar to that observed in human tissue. In a particularly preferred embodiment the cell line used is the 2.2.15 cell line, available from Dr. George Acs, Mount Sinai School of Medicine, New York, N.Y. 10029. This cell line is derived from the well-known human hepatoblastoma line HepG2, and is stably transfected with a plasmid containing the entire HBV genome. HBV DNA found in these cells is both episomal, in the form of relaxed circular, covalently closed copies of the HBV genome, and chromosomally integrated. HBV virions from 2.2.15 cells produce the full spectrum of clinical disease when injected into chimpanzees. Acs et al., *Proc. Natl. Acad. Sci. USA* 84: 4641 (1987). 2.2.15 cells are the standard cell line known to the art to measure the effects of antiviral compositions on HBV replication and have been shown to be an accurate model for all measured aspects of cellular HBV replication and for the response of HBV to antiviral agents which have been used in vivo. Korba et al., *Antiviral Res.* 19: 55–70 (1992).

An in vitro assay using an HBV-producing cell line preferably allows quantitative measurement of the effects of antiviral compositions on HBV replication. Suitable quantitative methods are well known in the art. In a preferred embodiment of the present invention, effects on HBV replication are determined by measuring levels of intracellular HBV DNA, RNA, and proteins, and extracellular HBV DNA and proteins. Isolation of DNA, RNA,and-protein samples from treated cells may be carried out by standard methods. For example, Triazol™, a commercial reagent available from Life Technologies, Inc. (Gaithersburg, Md.) allows preparation of DNA, RNA and protein in a single step. Standard methods for measuring the levels of nucleic acids will be readily apparent to the skilled practitioner, such as the use of Southern and Northern blotting techniques. See, for example, Sambrook et al., *Molecular Cloning: A Laboratory Manual*, Second Edition, Cold Spring Harbor Laboratory Press, (1989). In a particularly preferred embodiment, HBV DNA and RNA are prepared and measured by quantitative Southern and Northern blot hybridization techniques according to Korba et al., *Antiviral Res.* 15: 217 (1991), and Korba et al., (1992), supra. Levels of HBV proteins found in the extracellular medium of the 2.2.15 cells can be measured by techniques well known in the art. See, for example, CURRENT PROTOCOLS IN IMMUNOLOGY, Coligan et al., Eds. at 2.1.3. In a preferred embodiment, levels of HBV proteins in the extracellular medium are measured by an enzyme-linked immunoassay as described by Müller et al., *J. Infect. Dis.* 165: 929 (1992).

To ensure that any observed antiviral activity is due to specific effects of the antisense oligonucleotide under test, it is appropriate to use control experiments. Suitable control experiments will be apparent to the skilled practitioner, but in a preferred embodiment, 2',3'-dideoxycytidine (2',3'-ddC) is used as a positive assay standard. 2'3'-ddC is a selective, effective antiviral agent in 2.2.15 cells; it is known to inhibit production of both HBV virions and replicative intermediates.

For an antisense oligonucleotide to be therapeutically useful it is desirable that it exhibit not only antiviral activity but also low cellular toxicity. It is envisioned therefore that each compound will also be tested for its toxic effects on 2.2.15 cells. Suitable toxicity measurements are well known in the art, but in a preferred embodiment a neutral red dye uptake assay is used, as described in Korba et al. (1992), supra.

Antisense oligonucleotides can be tested for in vivo efficacy and safety in an animal model system. A preferred animal model is one in which the animal is infected with a virus as closely related as possible to the strains of HBV that are responsible for human disease. The virus should undergo an analogous viral replication cycle, and should produce clinical symptoms analogous to those observed in human chronic hepatitis. Several animal viruses are known in the Hepadnaviridae family, for example the ground squirrel hepatitis virus of California ground squirrels, the duck hepatitis B virus of Peking ducks, and the heron hepatitis B virus of German grey herons. In a preferred embodiment of the invention, the animal model is the woodchuck *Marmota Monax* infected with woodchuck hepatitis virus (WHV). See Tennant et al., "The Woodchuck Model of Hepatitis B. Virus Infection" In: THE LIVER, BIOLOGY AND PATHOBIOLOGY, 3rd Ed., Arias, J. M. et al., (Eds), Chapter 76. Korba et al., "Woodchuck Hepatitis Virus Infection as a Model for the Development of Antiviral Therapies Against HBV" In: VIRAL HEPATITIS AND LIVER DISEASE, Hollinger F. B. et al. (Eds.), 632. The morphology and genetic organization of WHV is very similar to HBV, and the replication cycle appears to be identical. Woodchucks infected with WHV suffer from chronic hepatitis, and also develop hepatocellular carcinoma (HCC) at a much higher rate than uninfected animals. These similarities of WHV and HBV have led to the proposal that WHV infection in woodchucks be adopted as the standard animal model for the development of new and improved strategies for the treatment of chronic viral hepatitis and HCC induced by HBV. See Tennant et al., supra.

B. Preparation of Antisense Oligonucleotides

As used in this disclosure the term "oligonucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The oligonucleotides of the -present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such oligonucleotides may be prepared by methods well-known in the art, for instance using commercially available machines and reagents available from Perkin-Elmer/Applied Biosystems (Foster City, Calif.).

Phosphodiester-linked oligonucleotides are particularly susceptible to the action of nucleases in serum or inside cells, and therefore in a preferred embodiment the oligonucleotides of the present invention are phosphorothioate or methyl phosphonate-linked analogues, which have been shown to be nuclease-resistant. See Stein et al., (1993), supra. Persons knowledgeable of this field will be able to select other linkages for use in the present invention.

C. Antiviral Effects of Antisense Oligonuclectides

The relative activity of antisense oligonucleotides directed against a specific gene is generally inversely proportional to its location relative to the AUG start codon of the target gene. In the prior art it is known that antisense oligonucleotides targeting sequences more than 60 bases downstream from the AUG start codon of chromosomally integrated HBV surface antigen [HBsAg] gene [S gene] sequences in HBsAg-producing PLC/PRF/5 cells are ineffective in inhibiting HBsAg production, while oligonucleotides placed within 20 bases of the AUG inhibit HBsAg production by 50% to 90%. In the present invention it is found that similar limitations hold for confluent cultures of 2.2.15 cells, a cell line in which over 95% of intracellular HBV DNA is episomal. As will be described in detail in Example 5, oligonucleotides targeting sequences more than 20 nucleotides upstream or downstream of the AUG have essentially no effect on HBV virion DNA and HBsAg production. Accordingly, it is preferred that an antisense oligonucleotide targeted at a specific HBV gene sequence be chosen such that the oligonucleotide hybridizes within approximately 25 bases of the AUG start codon of the gene.

To select the preferred length for an antisense oligonucleotide, a balance must be struck to gain the most favorable characteristics. Shorter oligonucleotides 10–15 bases in length readily enter cells, but have lower gene specificity. In contrast, longer oligonucleotides of 20–30 bases offer superior gene specificity, but show decreased kinetics of uptake into cells. See Stein et al., PHOSPHOROTHIOATE OLIGODEOXYNUCLEOTIDE ANALOGUES in "Oligodeoxynucleotides—Antisense Inhibitors of Gene Expression" Cohen, Ed. McMillan Press, London (1988). In a preferred embodiment this invention contemplates using oligonucleotides approximately 14 to 25 nucleotides long.

Oligonucleotides can be targeted around the AUG start codons of each of the different HBV coding regions, and their relative antiviral efficacies compared. For example, certain of the inventive oligonucleotides targeting the preS1 coding region are approximately as effective at inhibiting HBV virion production as are oligonucleotides targeting analogous regions of the S gene. For another example, oligonucleotides that target the HBeAg coding region or the HBV Pol gene do not inhibit HBV virion production in 2.2.15 cells. Oligonucleotides directed against HBeAg are, however, effective in inhibiting HBeAg production by 2.2.15 cells. The effect on HBV replication of candidate oligonucleotides directed against the HBV C gene can also be examined according to the invention. Oligonucleotides directed against regions close to, or overlapping, the AUG start codon of the C gene and that also encompass all, or part of, the single polyA signal in the HBV genome are the most effective at inhibiting HBV virion DNA and HBcAg production. Oligonucleotides directed primarily at the polyA signal are inactive or less active than those molecules directed at the beginning of the C gene.

The HBV encapsidation signal/sequence [$\epsilon$] is known to be essential for HBV replication. See Hirsch et al., *J. Virol.* 65: 3309 (1991). According to the present invention certain of the oligonucleotides directed at $\epsilon$ are the most highly effective molecules at inhibiting HBV production by 2.2.15 cells. The structure of the $\epsilon$ RNA transcript is thought to adopt a stem-loop secondary structure, containing both base-paired and unpaired sequences. See, for example, Knaus et al., *Nucl. Acids Res.* 21: 3967 (1993). The most active oligonucleotides among all the molecules tested are directed at the upper unpaired loop and the upper stem of the encapsidation sequence. Molecules that extend further into the lower stem are less active. Oligonucleotides targeting the upper stem demonstrate the importance of the inclusion of the nucleotides associated with the upper unpaired loop found in the active sequences. An oligonucleotide directed at the lower stem-and-loop structure is also effective at inhibiting HBV virion production. The relative activities of oligonucleotides directed at the unpaired nucleotides in the lower loop/bulge of $\epsilon$ show that these are also effective antiviral targets. Although the anti-$\epsilon$ oligonucleotides are targeted immediately upstream of the C gene, these molecules are relatively ineffective at lowering the intracellular levels of HBcAg.

In order to determine if the effects on HBV protein levels are correlated with the effects on HBV production, the relative levels of HBV virion DNA and HBV protein levels can be directly compared in cultures treated with the different anti-S or anti-C oligonucleotides. Strong correlation is observed between virion DNA and either HBsAg or HBcAg levels in cultures treated with either the anti-S or the anti-C oligonucleotides. A similar analysis can be performed for the anti-$\epsilon$ oligonucleotides. Because of the close proximity of $\epsilon$ to the beginning of the C gene sequence, the levels of HBcAg in cultures treated with the anti-$\epsilon$ oligonucleotides are compared to the levels of HBV virion DNA. Little correlation is observed between HBcAg levels and HBV virion DNA in these cultures. High concentrations of anti-$\epsilon$ oligonucleotides are able to effectively inhibit HBcAg levels, but at the $EC_{90}$ values [defined as 10-fold depression of HBV DNA levels relative to untreated (control) cultures] for virion DNA, little or no inhibition of HBcAg is observed.

D. Sequence Specificity and Toxicity

To test whether the antisense orientation of the oligonucleotides is the active antiviral component of these molecules, oligonucleotides complementary to the antisense oligonucleotides can be examined for anti-HBV activity.

The procedures described above and detailed in the examples below provide a basis for selecting oligonucleotides that selectively disrupt specific HBV functions under conditions of preexisting chronic viral replication. It is known that several different strains of HBV exist, and antisense oligonucleotides preferably are effective in inhibiting the replication of more than one strain of the virus. In accordance with this, most of the oligonucleotides revealed herein act at key control elements located in regions of the HBV genome known to be highly conserved among different sequenced isolates of HBV. For example, with the exception of specific HBe-negative mutants, the e nucleotide sequence is essentially 100% conserved among the published sequences of 35 different HBV isolates. A consensus HBV DNA ε sequence may be used to specify the antisense oligonucleotide sequences to ensure that molecules will be effective on any unspecified HBV genome.

E. Administration of Antisense Oligonucleotides to Subjects

Administration of an antisense oligonucleotide to a subject can be effected orally or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain oligonucleotide and about 10 mg of human serum albumin per milliliter of a phosphate buffer containing NaCl.

As much as 700 milligrams of antisense oligodeoxynucleotide has been administered intravenously to a patient over a course of 10 days (i.e., 0.05 mg/kg/hour) without signs of toxicity. Sterling, "Systemic Antisense Treatment Reported," *Genetic Engineering News* 12: 1, 28 (1992).

Other pharmaceutically acceptable excipients include non-aqueous or aqueous solutions and non-toxic compositions including salts, preservatives, buffers and the like. Examples of non-aqueous solutions are propylene glycol, polyethylene glycol, vegetable oil and injectable organic esters such as ethyloleate. Aqueous solutions include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art.

Antisense oligonucleotides may be administered by injection as an oily suspension. Suitable lipophilic solvents or vehicles include fatty oils, such as sesame oil, or synthetic fatty acid esters, such as ethyl oleate or triglycerides. Moreover, antisense oligonucleotides may be combined with a lipophilic carrier such as any one of a number of sterols including cholesterol, cholate and deoxycholic acid. A preferred sterol is cholesterol. Aqueous injection suspensions may contain substances which increase the viscosity of the suspension include, for example, sodium carboxymethyl cellulose, sorbitol, and/or dextran. Optionally, the suspension also contains stabilizers.

An alternative formulation for the administration of antisense PTN oligonucleotides involves liposomes. Liposome encapsulation provides an alternative formulation for the administration of antisense PTN oligonucleotides. Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46: 618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s). See, for example, Machy et al., LIPOSOMES IN CELL BIOLOGY AND PHARMACOLOGY (John Libbey 1987), and Ostro et al., *American J. Hosp. Pharm.* 46: 1576 (1989). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N.Y. Acad. Sci.* 446: 368 (1985).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biohys. Acta* 1150: 9 (1993) These Stealth® liposomes have an increased circulation time and an improved targeting to tumors in animals. Woodle et al., *Proc. Amer. Assoc. Cancer Res.* 33: 2672 (1992). Human clinical trials are in progress, including Phase III clinical trials against Kaposi's sarcoma. Gregoriadis et al., *Drugs* 45: 15 (1993).

Antisense oligonucleotides can be encapsulated within liposomes using standard techniques. A variety of different liposome compositions and methods for synthesis are known to those of skill in the art. See, for example, U.S. Pat. No. 4,844,904, U.S. Pat. No. 5,000,959, U.S. Pat. No. 4,863,740, and U.S. Pat. No. 4,975,282, all of which are hereby incorporated by reference.

Liposomes can be prepared for targeting to particular cells or organs by varying phospholipid composition or by inserting receptors or ligands into the liposomes. For instance, antibodies specific to liver associated antigens may be incorporated into liposomes, together with antisense oligonucleotides, to target the liposome more effectively to the liver. See, for example, Zelphati et al., *Antisense Research and Development* 3: 323–338 (1993), describing the use "immunoliposomes" containing antisense oligonucleotides for human therapy.

In general, the dosage of administered liposome-encapsulated antisense oligonucleotides will vary depending upon such factors as the patient's age, weight, height, sex, general medical condition and previous medical history. Dose ranges for particular formulations can be determined by using a suitable animal model.

The present invention, thus generally described, will be understood more readily by reference to the following examples, which are provided by way of illustration and are not intended to be limiting of the present invention.

EXAMPLE 1

Cell Culture

Details of the design of the antiviral procedure and the growth conditions for the HBV-producing, human hepatoblastoma cell line, 2.2.15 cells (Sells et al., *J. Virol.* 62: 2836 (1989) have been previously described (Korba et al., 1991, supra). The standardized culture assay (Korba et al., *Antiviral Res.* 19: 55 (1992)) uses confluent cultures of 2.2.15 cells which chronically produce infectious HBV, that causes disease in chimpanzees (Acs et al., *Proc. Natl. Acad. Sci. USA* 84: 4641–44 (1987). This cell line has been shown to be an accurate model for all measured aspects of cellular HBV replication and for the response of HBV to several antiviral agents which have been used in vivo. See, for example, Korba et al., 1991), supra; Korba et al., (1992), supra; Lampertico et al., *Hepatology* 13:422 (1991); Doong et al., *Proc. Nat'l Acad. Sci. USA* 93:8495 (1991); Cheng et al., *J. Biol. Chem.* 267:22414 (1992); Tyrrell et al., *Hepatology* 18(2):112A (1993). HBV DNA replication and gene expression in this cell line is at stable, maximal levels only in confluent cultures. Briefly, confluent cultures of 2.2.15 cells, maintained in RPMI1640 (with 4% fetal bovine serum) on 96-well flat-bottomed plates, were treated with oligonucleotides (0.3–20 $\mu$M, 3–6 cultures each) daily for 9 consecutive days. Stock cultures of 2.2.15 cells were routinely passaged only 3–4 times after recovery from cryopreservation.

In these studies, 2',3'-dideoxycytidine, a selective and effective antiviral agent in 2.2.15 cells was used as a positive assay standard.

EXAMPLE 2

Preparation of Oligonucleotides

Phosphorothioate-substituted oligonucleotides were produced using an Applied Biosystems DNA Synthesizer (Model 384B). The base sequence used to synthesize the oligonucleotides for these studies is the consensus sequence for HBV/ayw. Galibert et al., *Nature* 281: 646 (1979). The HBV genome in 2.2.15 cells has been previously identified to be subtype HBV/ayw. Sells et al., supra, Acs et al., supra.

EXAMPLE 3

Analysis of HEV Nucleic Acids and Proteins

HBV virion DNA in culture medium, and intracellular HBV RI and HBV RNA levels were determined by quantitative blot hybridization analyses: dot, Southern and Northern blot, respectively. See Sambrook et al., supra.

Nucleic acids were prepared by previously described procedures. Korba et al., *Hepatol*, 9: 461 (1989). Before culture media samples were aliquoted for HBV DNA analysis, each sample was centrifuged for 1 min at maximum speed (14000×g) in a microcentrifuge.

The probe used for the hybridization analyses was a $^{32}$P-labelled, gel purified, 3.2-Kb Eco RI HBV DNA fragment from plasmid AM12. Korba et al., *J. Virol.* 58: 1 (1986).

HBV DNA concentrations were determined by comparisons to HBV standards using an AMBIS beta scanner (AMBIS systems, San Diego, Calif.) as previously described (Korba et al., *Hepatology* 9: 461 (1989); Korba et al., *Antiviral Res.* 15: 217 (1991)).

Integrated HBV DNA, which remains at a stable level per cell during the treatment period, was used to quantitate the amount of cellular DNA transferred in each Southern gel lane. Korba et al., (1992) supra.

For the HBV RNA analyses, the levels of $\beta$-actin RNA (Cleveland et al., *Cell*, 20: 95 (1980)) were used to quantitate the amount of cellular RNA transferred in each Northern gel lane. Korba et al., (1991) supra. Previous examinations of $\beta$-actin specific RNA in confluent cultures of 2.2.15 cells demonstrated a steady state level of approximately 1.0 pg $\beta$-actin RNA/$\mu$g unfractionated cellular RNA.

$EC_{90}$ values were determined by linear regression. $EC_{90}$ values are used for comparison since, in this culture system, DNA levels within 3-fold of control values are not generally statistically significant. Korba et al., (1992) supra.

Values for HBV proteins were determined by semi-quantitative EIA. See Muller et al., *J. Infect. Dis.* 165: 929 (1992). For the EIA analyses, test samples were diluted (2 to 10-fold) so that the assay values produced were within the linear dynamic range of the EIA assays. Standard curves using serial dilutions of positive assay controls were included in each set of EIA analyses.

Cultures for HBV RNA were maintained on 6-well plates, cultures for HBV virion DNA analyses were maintained on either 96 or 24-well plates, and cultures for all other HBV parameters were maintained on 24-well plates.

EXAMPLE 4

Toxicity Measurements

Toxicity was determined by the inhibition of the uptake of neutral red dye (Finter, *J. Gen. Virol.* 5: 419 (1969). Cells were grown to confluence in 96-well flat-bottomed tissue culture plates and treated with oligonucleotides as described above. Four concentrations of each compound were assayed, each in triplicate cultures, in 3 to 10-fold steps. Twenty-four hours following the final addition of compound, culture medium was removed and 0.2 ml of DPBS containing 0.01% neutral red dye (Sigma, Inc.) was added to each culture well. The cells were then returned to the tissue culture incubator for 2 h. The dye was removed, the cells were washed once with DPBS (0.2 ml/well), and then 0.2 ml of 50% ETOH/1% glacial acetic acid was added to each well. Following 30 min of gentle mixing on a rotary platform at room temperature, absorbance at 510 nanometers [$A_{510}$] was determined. On each 96-well plate, wells containing no cells were used to correct for possible light-scattering effects. Untreated control cultures were also maintained on each 96-well plate. $CC_{50}$ values (50% cytotoxic concentration: drug concentration which induces a 50% inhibition of dye uptake versus control cultures) were calculated by linear regression analysis, as described above.

EXAMPLE 5

Antiviral Activity of Antisense Oligonucleatides

A. Oligonucleotides Targeting the HBV S Gene

Eleven oligonucleotides, designed to be complementary to the S gene of the ayw subtype of HBV, were synthesized. The location of the target site and the antiviral activity of each oligonucleotide are shown in FIG. 1. The open box denotes the AUG start codon of the S gene. Coordinates are nucleotides relative to the "A" (nucleotide "+1") of the AUG start codon. Lines indicate the relative position of the different oligonucleotides; numbers above each line indicate the length (in nucleotides) of each molecule. The designation ">20" indicates that no inhibition of HBV virion DNA or HBsAg (relative to control cultures) was observed for the indicated oligonucleotide at concentrations up to 20 μM. The nucleotide sequences of each oligonucleotide are those contained in a previously published sequence of HBV/ayw. Galibert et al., Nature 281: 646 (1979). In this numbering scheme, nucleotide "1" is the 1st base following the unique Eco RI cleavage site. The coordinates of the 1st nucleotide in each antisense oligonucleotide are as follows: (S1) (SEQ ID NO:1) 160, (S2) (SEQ ID NO:3) 160, (S3) (SEQ ID NO:4) 157, (S4) (SEQ ID NO:5) 157, (S5) (SEQ ID NO:6) 177, (S6) (SEQ ID NO:7) 197, (S7) (SEQ ID NO:8) 217, (S8) (SEQ ID NO:9) 145, (S9) (SEQ ID NO:10) 125, (S10) (SEQ ID NO:11) 105, (S11) (SEQ ID NO:12) 151. The relative activities of the oligonucleotides was found to be directly proportional to their relative distance from the AUG start codon.

Figure 2:
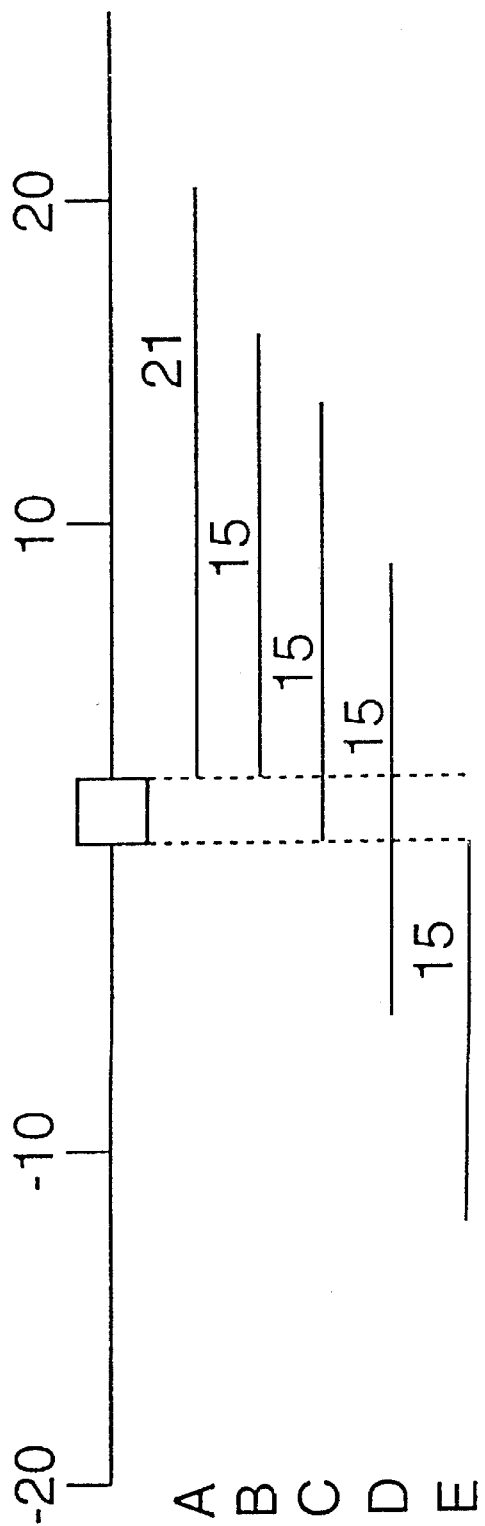
FIG. 2 shows the effect on virion production of antisense oligonucleotides targeted at three HBV genes: preS1 (preS1), e (HBeAg), POL (polymerase). The locations of the oligonucleotides relative to the AUG start codon (shown as an open box) of the genes or coding regions are shown. See legend to FIG. 1 for other details.

In a similar fashion, 15 antisense oligonucleotides were synthesized to be targeted to (i) the region upstream of the S gene which encodes for pres1, (ii) the region upstream of the HBV core antigen [HBcAg] gene [C gene] which encodes for the HBV e antigen [HBeAg], and (iii) the HBV polymerase [pol] gene. The location of each oligonucleotide relative to the initiation codon (shown as an open box) of each gene is shown in FIG. 2. The coordinates of the 1st nucleotide in each antisense oligonucleotide are as follows: pres1, (A) (SEQ ID NO:13) 2853, (B) (SEQ ID NO:14) 2853, (C) (SEQ ID NO:15) 2850, (D) (SEQ ID NO:16) 2844, (E) (SEQ ID NO:17) 2838; HBe, (A) (SEQ ID NO:19) 1818, (B) (SEQ ID NO:21) 1818, (C) (SEQ ID NO:22) 1815, (D) (SEQ ID NO:23) 1809, (E) (SEQ ID NO:24) 1803; POL, (A) (SEQ ID NO:25) 2311, (B) (SEQ ID NO:27) 2311, (C) (SEQ ID NO:28) 2308, (D) (SEQ ID NO:29) 2302, (E) (SEQ ID NO:30) 2296.

Figure 3:
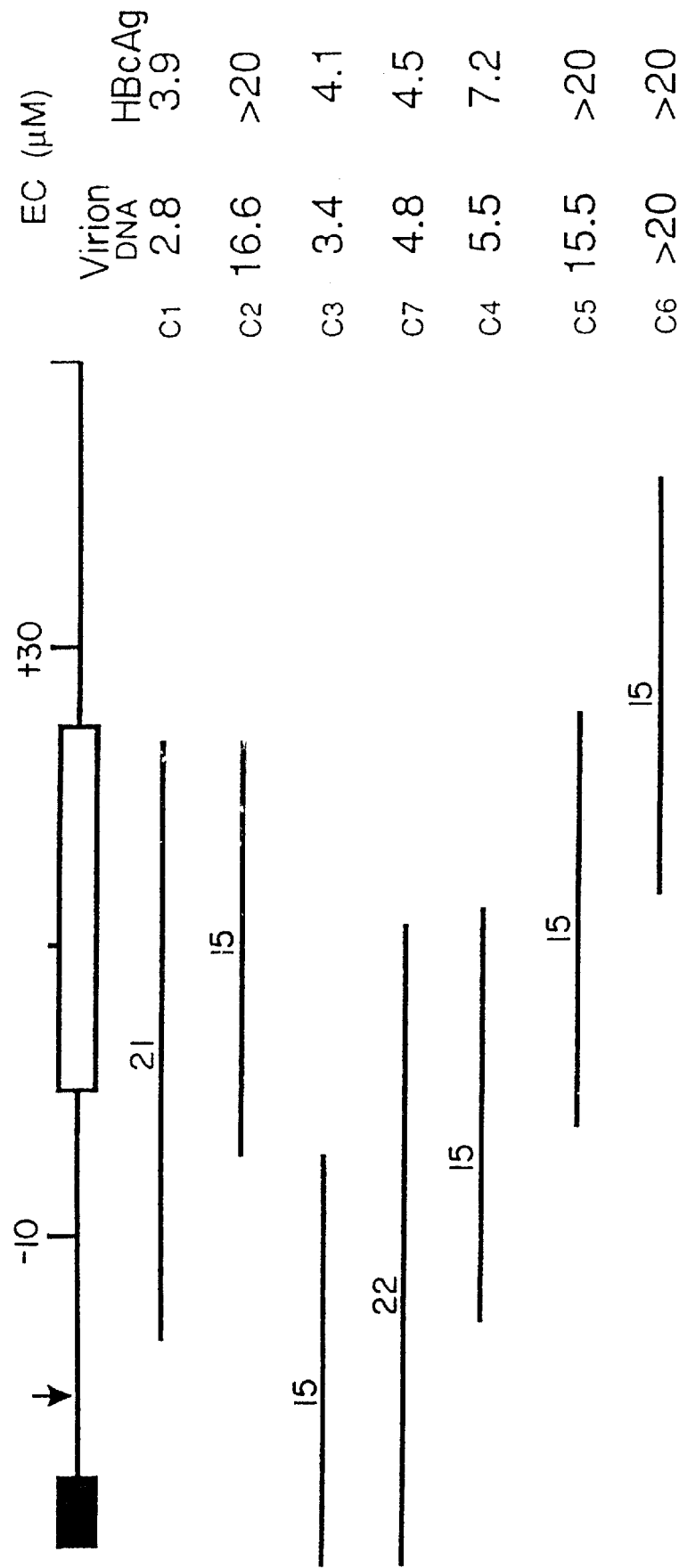
FIG. 3 shows the effect of oligonucleotides targeting the C gene. The filled box denotes the AUG start codon for the C gene, the open box denotes the location of the single HBV polyadenylation signal/sequence, and the arrow indicates the location of the last base in the $\epsilon$ stem-and-loop structure. See legend to FIG. 1 for other details.

Similarly, five oligonucleotides were synthesized, targeting the C gene, and the results obtained are shown in FIG. 3. The filled box denotes the AUG start codon for the C gene, the open box denotes the location of the single HBV polyadenylation signal/sequence, and the arrow indicates the location of the last base in the ε stem-and-loop structure. Coordinates of the first nucleotides in the oligonucleotides displayed in this figure are: (C1,C4) (SEQ ID NOS 31 and 35) 1910, (C2) (SEQ ID NO:33) 1916, (C3,C7) (SEQ ID NOS 34 and 38) 1903, (C5) (SEQ ID NO:36) 1917, (C6) (SEQ ID NO:37) 1925.

Figure 4:
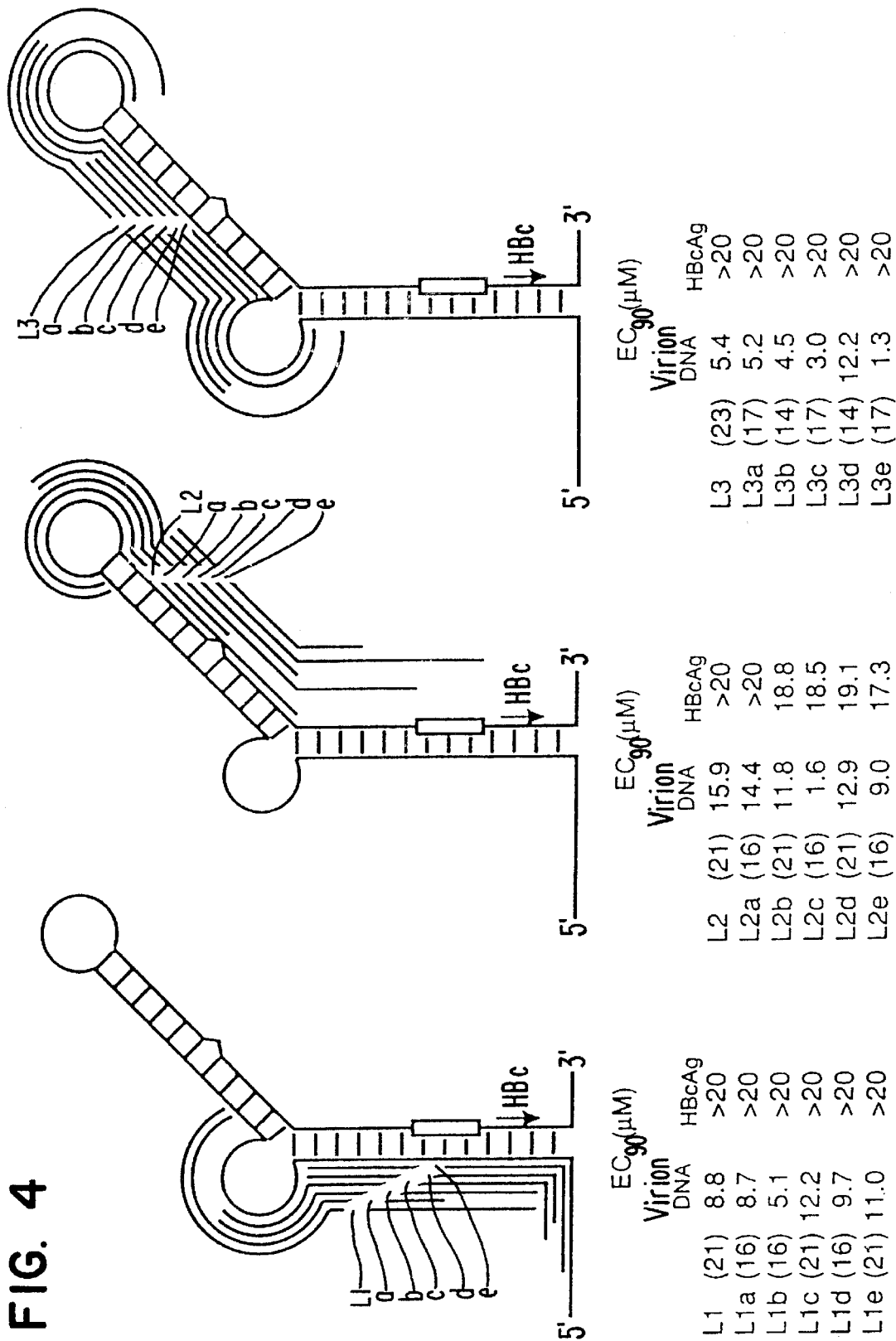
FIG. 4 shows the effect of oligonucleotides targeting the $\epsilon$ packaging signal. The open box denotes the AUG start codon for the C gene. The sizes of each oligonucleotide are indicated in parenthesis. In the numbering scheme used in this study, the nucleotide located at the bottom of the 5' side of the lower stem is nucleotide 1849 and is paired with nucleotide 1909.

FIG. 4 shows the results obtained with 15 oligonucleotides targeting the ε packaging signal. The open box denotes the AUG start codon for the C gene. The sizes of each oligonucleotide are indicated in parenthesis. In the numbering scheme used in this study, the nucleotide located at the bottom of the 5' side of the lower stem is nucleotide 1849 and is paired with nucleotide 1909. Coordinates of the first nucleotides in the oligonucleotides displayed in this figure are: (L1) (SEQ ID NO:39) 1849, (L1a) (SEQ ID NO:40) 1854, (L1b) (SEQ ID NO:41) 1849, (L1c) (SEQ ID NO:42) 1844, (L1d) (SEQ ID NO:43) 1846, (L1e) (SEQ ID NO:44) 1841, (L2) (SEQ ID NO:45) 1879, (L2a) (SEQ ID NO:46) 1879, (L2b) (SEQ ID NO:47) 1884, (L2c) (SEQ ID NO:48) 1884, (L2d) (SEQ ID NO:49) 1887, (L2e) (SEQ ID NO:50) 1887, (L3) (SEQ ID NO:51) 1862, (L3a) (SEQ ID NO:52) 1865, (L3b) (SEQ ID NO:53) 1865, (L3c) (SEQ ID NO:54) 1862, (L3d) (SEQ ID NO:55) 1868, (L3e) (SEQ ID NO:56) 1868.

Figure 5A:
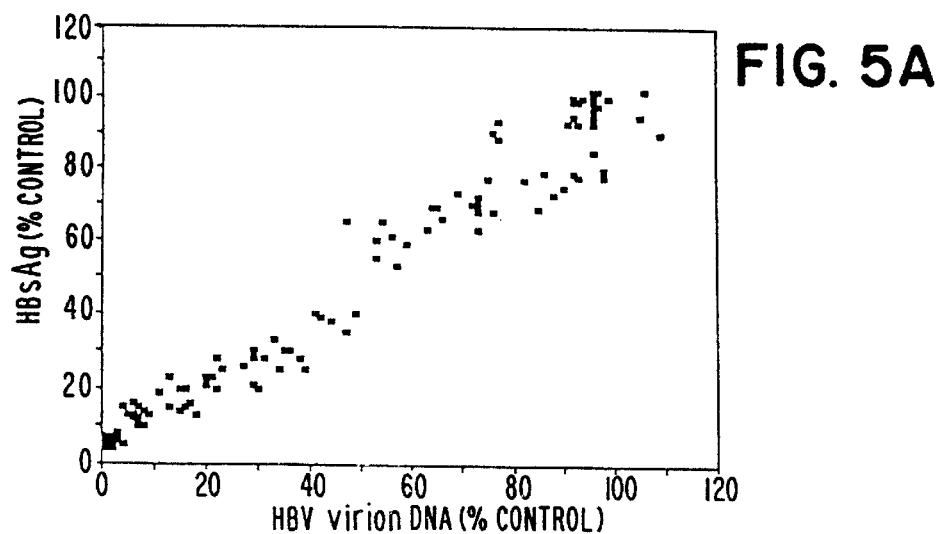
FIG. 5 (Parts A–C) shows a comparison of HBV virion and HBV protein levels for cultures treated with antisense oligonucleotides. The relative levels (as compared to control (untreated) cultures) of HBV virion DNA and either HBsAg (PANEL A) or HBCAg (PANELS B AND C) in cultures treated with various concentrations of different antisense oligonucleotides were directly compared. Each plotted point represents an average of values obtained from 3 to 4 separate cultures. PANEL A: cultures treated with anti-S oligonucleotides, PANEL B: cultures treated with anti-C oligonucleotides, PANEL C: cultures treated with anti-$\epsilon$ oligonucleotides.
Figure 5B:
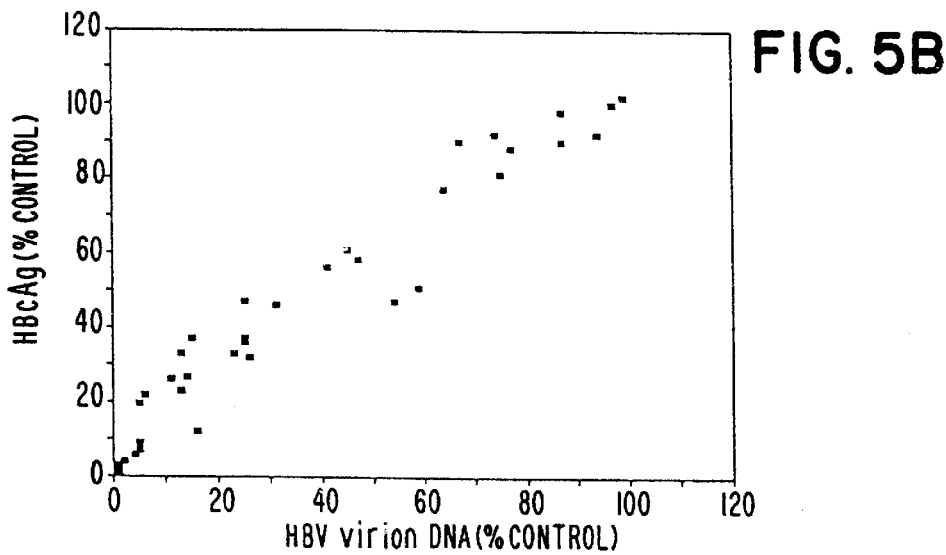
Figure 5C:
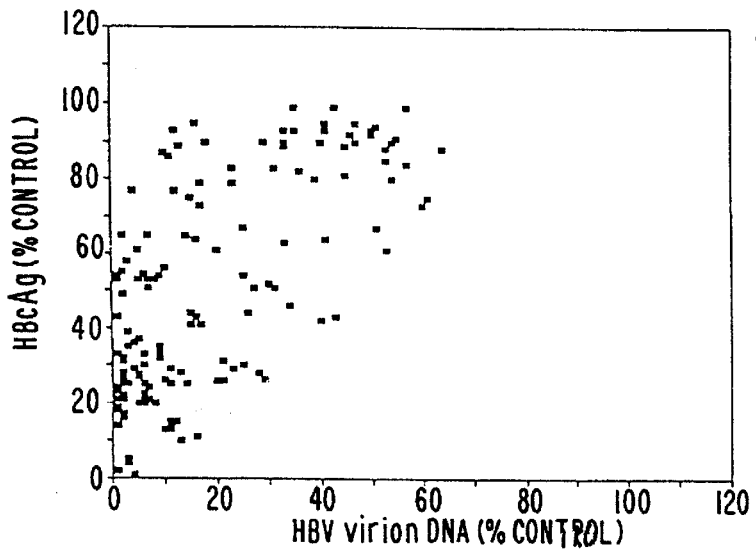

FIG. 5 shows a comparison of HBV virion and HBV protein levels for cultures treated with antisense oligonucleotides. The relative levels (as compared to control (untreated) cultures) of HBV virion DNA and either HBsAg (PANEL A) or HBcAg (PANELS B AND C) in cultures treated with various concentrations of different antisense oligonucleotides were directly compared. Each plotted point represents an average of values obtained from 3 to 4 separate cultures. PANEL A: cultures treated with anti-S oligonucleotides, PANEL B: cultures treated with anti-C oligonucleotides, PANEL C: cultures treated with anti-ε oligonucleotides.

Figure 6:
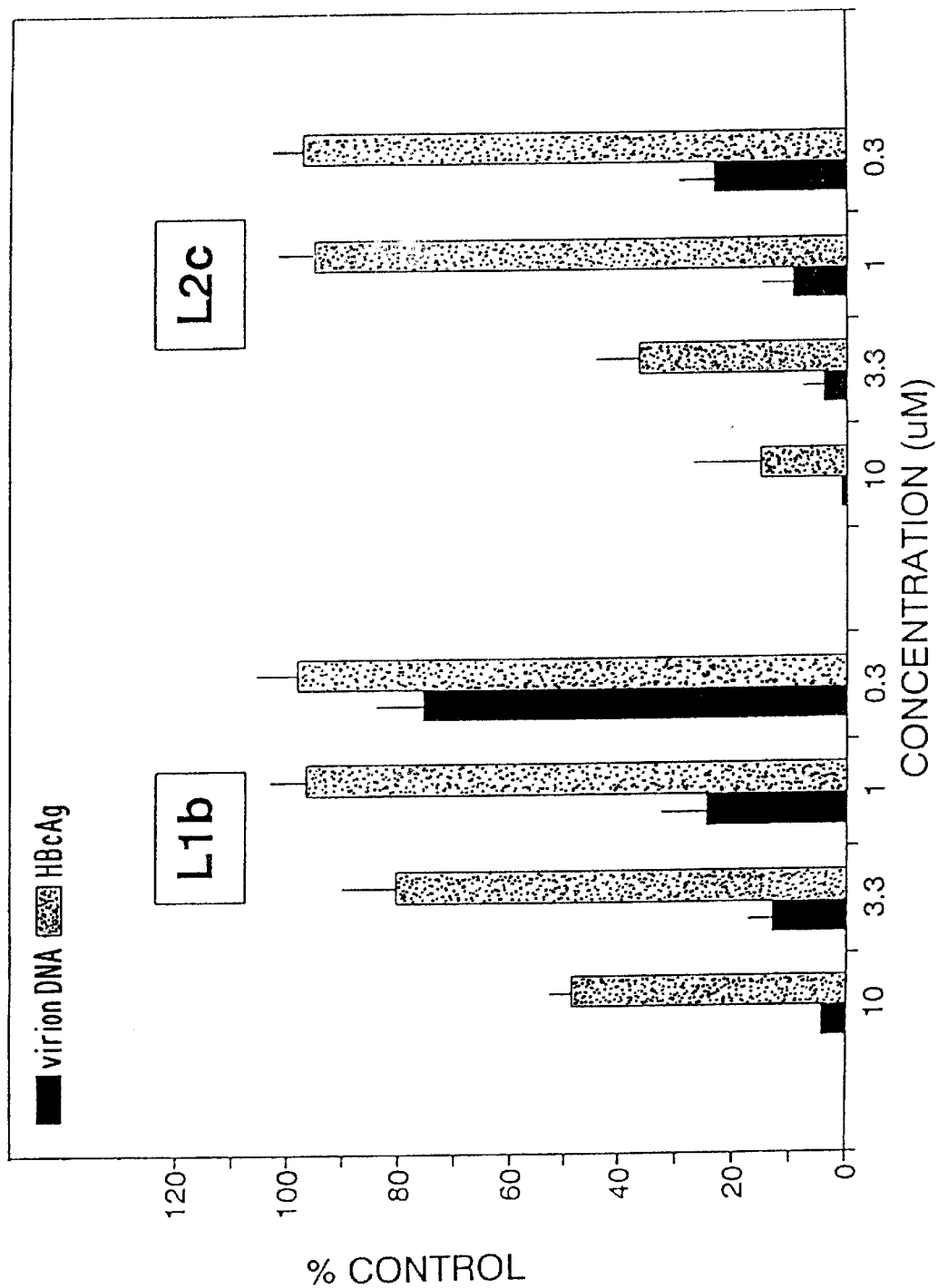
FIG. 6 shows the effect of anti-$\epsilon$ antisense oligonucleotide concentration on HBV virion DNA and HBcAg levels. The relative levels (as compared to control (untreated) cultures) of HBV virion DNA and HBcAg following treatment with different cultures of oligonucleotides L1b or L2c are displayed. Bars represent an average of values obtained from 4 to 12 separate cultures from 2 to 3 experiments. Lines indicate standard deviations.

FIG. 6 shows the effect of anti-ε antisense oligonucleotide concentration on HBV virion DNA and HBcAg levels. The relative levels (as compared to control (untreated) cultures) of HBV virion DNA and HBcAg following treatment with different cultures of oligonucleotides L1b (SEQ ID NO:41) or L2c (SEQ ID NO:48) are displayed. Bars represent an average of values obtained from 4 to 12 separate cultures from 2 to 3 experiments. Lines indicate standard deviations.

Five oligonucleotides complementary to five of the antisense oligonucleotides were synthesized and tested for antiviral activity. None of these five "sense" oligonucleotides had any measurable effect on HBV production in 2.2.15 cells at concentrations up to 20 μM, indicating that the antiviral activities of the active molecules are specific to the antisense sequences. See Table 1 (SEQ ID NOS 2, 18, 20, 26, and 32).

None of 8 oligonucleotides examined for toxicity (C1 (SEQ ID NO:31), L1c (SEQ ID NO:42), L2b (SEQ ID NO:47), L3e (SEQ ID NO:56), S1 (SEQ ID NO:1), PS1A (SEQ ID NO:13), EA (SEQ ID NO:19), and PA (SEQ ID NO:25)) caused any significant inhibition of neutral red uptake by 2.2.15 cells at concentrations of up to 500 μM, a level more than 100-fold higher than most of the effective antiviral concentrations (data not shown).

The activities of the 51 antisense and 5 sense oligonucleotides tested are summarized in Table 1, which shows the effects of all the oligonucleotides (SEQ ID NOS 1–56) on the levels of: HBV DNA in the extracellular medium (VIR. DNA); intracellular viral replicative intermediates (HBV RI); intracellular viral RNA (HBV RNA); HBV surface antigen protein (HBsAg); HBV e antigen protein (HBeAg); and HBV core antigen protein (HBcAg).

TABLE 1

Activity of oligonucleotides
EC90 (μM, 9 days of treatment)(ND, not determined)

| SEQ ID NO: | NAME | ORIENTATION | SEQUENCE (3'→5') | VIR. DNA | HBV RI | HBV RNA | HBsAg | HBeAg | HBcAg |
|---|---|---|---|---|---|---|---|---|---|
| 1 | S1 | antisense | GAGAACATCACATCAGGATTC | 3 | >20 | >20 | 2 | >20 | >20 |
| 2 | S1S | sense | GAATCCTGATGTGATGTTCTC | >20 | >20 | ND | >20 | >20 | >20 |
| 3 | S2 | antisense | GAGAACATCACATCAG | 2.8 | ND. | ND | 1.8 | >20 | >20 |
| 4 | S3 | antisense | ATGGAGAACATCACATCAGGA | 3.1 | ND | ND | 1.5 | >20 | >20 |
| 5 | S4 | antisenso | ATGGAGAACATCACAT | 2.8 | ND | NO | 1.7 | >20 | >20 |

TABLE 1-continued

Activity of oligonucleotides
EC90 (μM, 9 days of treatment)(ND, not determined)

| SEQ ID NO: | NAME | ORIENTATION | SEQUENCE (3'→5') | VIR. DNA | HBV RI | HBV RNA | HBsAg | HBeAg | HBcAg |
|---|---|---|---|---|---|---|---|---|---|
| 6 | S5 | antisense | TCCTAGGACCCCTTCT | 9.8 | ND | ND | 11 | >20 | >20 |
| 7 | S6 | antisense | GTTACAGGCGGGGTTU | >20 | ND | ND | >20 | >20 | >20 |
| 8 | S7 | antisense | TTGTTGACAAGAATCC | >20 | ND | ND | >20 | >20 | >20 |
| 9 | S8 | antisense | GGACCCTGCGCTGAACATG | 6.9 | ND | ND | 3.2 | >20 | >20 |
| 10 | S9 | antisense | CAATCTTCTCGAGGAT | >20 | ND | ND | >20 | >20 | >20 |
| 11 | S10 | antisense | TGTTCTGATCCCTTAT | >20 | ND | ND | >20 | >20 | >20 |
| 12 | S11 | antisense | CTGAACATGGAGAAC | 5.1 | ND | ND | 2.6 | >20 | >20 |
| 13 | PS1A | antisense | GGGCAGAATCTTTCCACCAGC | 6.6 | >20 | >20 | >20 | >20 | >20 |
| 14 | PS1B | antisense | GGGCAGAATCTTTCC | 6 | ND | ND | >20 | >20 | >20 |
| 15 | PS1C | antisense | ATGGGGCAGAAT | 6.2 | ND | ND | >20 | >20 | >20 |
| 16 | PS1D | antisense | TACAGCATGGGGCAG | 8.7 | ND | ND | >20 | >20 | >20 |
| 17 | PS1E | antisense | AAGATCTACAGCATG | 12 | ND | ND | >20 | >20 | >20 |
| 18 | PS1S | sense | GCTGGTGGAAAGATTCTGCCC | >20 | ND | ND | >20 | >20 | >20 |
| 19 | EA | antisense | CAACTTTTCACCTCGCCTA | >20 | >20 | >20 | >20 | 6.8 | >20 |
| 20 | E1S | sense | TAGGCGAGGTGAAAAAGTTG | >20 | >20 | ND | >20 | >20 | >20 |
| 21 | EB | antisense | CAACTTTTTCACCT | >20 | ND | ND | >20 | 11.3 | >20 |
| 22 | EC | antisense | ATGCAACTTTTTCAC | >20 | ND | ND | >20 | 5.4 | >20 |
| 23 | ED | antisense | AGCACCATGCAACTT | >20 | ND | ND | >20 | 5 | >20 |
| 24 | EE | antisense | CGCACCAGCACCATG | >20 | ND | ND | >20 | 9.8 | >20 |
| 25 | PA | antisense | CCCCTATCCTATCAACACTTC | >20 | >20 | >20 | >20 | >20 | >20 |
| 26 | P1S | sense | GAAGTGTTGATAGGATAGGGG | >20 | >20 | ND | >20 | >20 | >20 |
| 27 | PB | antisense | CCCCTATCCTATCAA | >20 | ND | ND | >20 | >20 | >20 |
| 28 | PC | antisense | ATGCCCCTATCCTAT | >20 | ND | ND | >20 | >20 | >20 |
| 29 | PD | antisense | CACCAAATGCCCCTA | >20 | ND | ND | >20 | >20 | >20 |
| 30 | PE | antisense | ATAGACCACCAAATG | >20 | ND | ND | >20 | >20 | >20 |
| 31 | C1 | antisense | TCGACCCTTATAAAGAATTTG | 2.8 | 13.5 | >20 | >20 | >20 | 3.9 |
| 32 | C1S | sense | CAAATTCTATAAGGGTCGA | >20 | >20 | ND | >20 | >20 | >20 |
| 33 | C2 | antisense | CTTATAAAGAATTTG | 16.6 | ND | ND | >20 | >20 | >20 |
| 34 | C3 | antisense | ATGGACATCGACCCT | 3.4 | ND | ND | >20 | >20 | 4.1 |
| 35 | C4 | antisense | TCGACCCTTATAAAG | 5.5 | ND | ND | >20 | >20 | 7.2 |
| 36 | C5 | antisense | TTATAAAGAATUGG | >20 | ND | ND | >20 | >20 | >20 |
| 37 | C6 | antisense | GAATTTGGAGCTACT | >20 | ND | ND | >20 | >20 | >20 |
| 38 | C7 | antisense | ATGGACATCGACCCT-TATAAAG | 3.8 | ND | ND | >20 | >20 | 4.5 |
| 39 | L1 | antisense | ACAAGTACTGGATGACAAGTT | 8.8 | ND | >20 | >20 | >20 | >20 |
| 40 | L1a | antisense | TACAGGATGACAAGTT | 8.7 | ND | ND | >20 | >20 | >20 |
| 41 | L1b | antisense | ACAAGTACAGGATGAC | 5.1 | 12.3 | >20 | >20 | >20 | >20 |
| 42 | L1c | antisense | GAGAACAAGTACAGGATGAC | 12.2 | ND | ND | >20 | >20 | >20 |
| 43 | L1d | antisense | AGAACAAGTACAGGAT | 9.7 | ND | ND | >20 | >20 | >20 |
| 44 | L1e | antisense | AGTAGAGAACAAGTACAGGAt | 11 | ND | ND | >20 | >20 | >20 |
| 45 | L2 | antisense | TCGACACGGAACCCACCGAAA | 15.9 | ND | ND | >20 | >20 | >20 |
| 46 | L2a | antisense | TCGACACGGAACCCAC | 14.4 | ND | NO | >20 | >20 | >20 |
| 47 | L2b | antisense | ACGGAACCCACCGAAACCCA | 11.8 | ND | >20 | >20 | | 18.8 |
| 48 | L2c | antisense | ACGGAACCCACCGAAA | 1.6 | 5.1 | >20 | >20 | >20 | 18.5 |
| 49 | L2d | antisense | GAACCCACCGAAACCCTAGTA | 12.9 | ND | ND | >20 | >20 | 19.1 |
| 50 | L2e | antisense | GAACCCACCGAAACCC | 9 | ND | ND | >20 | >20 | 17.3 |
| 51 | L3 | antisense | GACAAGUCGGAGGTTCGA-CACG | 5.4 | ND | ND | >20 | >20 | >20 |
| 52 | L3a | antisense | AAGTTCGGAGGTTCGAC | 5.2 | ND | ND | >20 | >20 | >20 |
| 53 | L3b | antisense | AAGTTCGGAGGTTC | 4.5 | ND | ND | >20 | >20 | >20 |
| 54 | L3c | antisense | GACAAGTTCGGAGGTTC | 3 | ND | ND | >20 | >20 | >20 |
| 55 | L3d | antisense | TTCGGAGGTTCGAC | 12.2 | ND | ND | >20 | >20 | >20 |
| 56 | L3e | antisense | TTCGGAGGTTCGACACG | 1.3 | 4.7 | >20 | >20 | >20 | >20 |

What is claimed is:

1. A method for treating an HBV infection in a patient, comprising administering to said patient an effective amount of a single stranded antisense oligonucleotide sufficient to bind the E encapsidation sequence of the single stranded mRNA intermediate derived from the HBV DNA genome to inhibit HBV replication.

2. The method of claim 1, wherein said HBV-related function is selected from the group consisting of transcription, translation, encapsidation, replication, and release from said host cell.

3. The method of claim 1, wherein said oligonucleotide is from about 14 to about 25 bases long.

4. The method of claim 1, wherein said oligonucleotide is directed against a lower portion of the stem-and-loop structure of said e sequence of said mRNA as depicted in FIG. 4.

5. The method of claim 1, wherein said oligonucleotide is directed against an upper unpaired loop and the upper stem of said e sequence of said mRNA as depicted in FIG. 4.

6. The method of claim 1, wherein said oligonucleotide comprises a sequence selected from the group TTGAACAGTAGGTCATGAACA, TTGAACAGTAGGACAT, CAGTAGGACATGAACA, CAGTAGGACATGAACAAGAG, TAGGACATGAACAAGA, TAGGACATGAACAAGAGATGA, AAAGCCACCCAAGGCACAGCT, CACCCAAGGCACAGCT, ACCCCAAAGCCACCCAAGGCA, AAAGCCACCCAAGGCA, ATGATCCCAAAGCCACCCAAG, CCCAAAGCCACCCAAG, GCACAGCTTGGAGGCTTGAACAG, CAGCTTGGAGGCTTGAA, CTTGGAGGCTTGAA, CTTGGAGGCTTGAACAG, CAGCTTGGAGGCTT, GCACAGCTTGGAGGCTT (SEQ ID NOS 39–56, respectively).

7. The method of claim 1, wherein said oligonucleotide is encapsulated within a liposome.

8. A pharmaceutical preparation comprising a composition for inhibiting replication of hepatitis B virus (HBV) in a host cell, comprising a single-stranded antisense oligonucleotide that (i) binds the ε encapsidation sequence of a mRNA intermediate derived from the HBV DNA genome and the (ii) modulates as HBV-related function in said host cell, in a pharmaceutically acceptable sterile vehicle.

9. A method for treating chronic HBV infections in a patient, comprising administering to said patient an amount of a single-stranded antisense oligonucleotide sufficient to bind to an mRNA derived from the HBV DNA genome and modulate an HBV-related function, wherein said oligonucleotide is selected from the group containing: CTTAGGACTACACTACAAGAG, GACTACACTACAAGAG, AGGACTACACTACAAGAGGTA, TACACTACAAGAGGTA, TCTTCCCCAGGATCCT, GTACAAGTCGCGTCCCAGG, CAAGAGGTACAAGTC, CGACCACCTTTCTAAGACGGG, CCTTTCTAAGACGGG, TAAGACGGGGTA, GACGGGGTACGACAT, GTACGACATCTAGAA, GTTTAAGAAATATTCCCAGCT, GTTTAAGAAATATTC, TCCCAGCTACAGGTA, GAAATATTCCCAGCT, and GAAATATTCCCAGCTACAGGTA (SEQ ID NOS 1, 3, 4, 5, 6, 9, 12, 13, 14, 15, 16, 17, 31, 33, 34, 35, and 38, respectively).

10. A method for inhibiting the replication of hepatitis B virus (HBV) in an infected cell comprising administering to the cell an effective amount of a single stranded antisense oligonucleotide sufficient to bind the encapsidation sequence of the single stranded mRNA intermediate derived from the HBV DNA genome and inhibit an HBV-related function.

11. The method of claim 10, wherein said HBV-related function is selected from the group consisting of transcription, translation, encapsidation, replication and release from the host cell.

12. The method of claim 10, wherein said oligonucleotide is from about 14 to about 25 bases long.

13. The method of claim 10, wherein said oligonucleotide is directed against a lower portion of the stem-and-loop structure of said ε sequence of said mRNA as depicted in FIG. 4.

14. The method of claim 10, wherein said oligonucleotide is directed against an upper unpaired loop and the upper stem of said ε sequence of said mRNA as depicted in FIG. 4.

15. The method of claim 10, wherein said oligonucleotide comprises a sequence selected from the group consisting of TTGAACAGTAGGTCATGAACA (SEQ ID NO:39), TTGAACAGTAGGACAT (SEQ ID NO:40), CAGTAGGACATGAACA (SEQ ID NO:41), CAGTAGGACATGAACAAGAG (SEQ ID NO:42), TAGGACATGAACAAGA (SEQ ID NO:43), TAGGACATGAACAAGAGATGA (SEQ ID NO:44), AAAGCCACCCAAGGCACAGCT (SEQ ID NO:45), CACCCAAGGCACAGCT (SEQ ID NO:46), ACCCCAAAGCCACCCAAGGCA (SEQ ID NO:47), AAAGCCACCCAAGGCA (SEQ ID NO:48), ATGATCCCAAAGCCACCCAAG (SEQ ID NO:49), CCCAAAGCCACCCAAG (SEQ ID NO:50), GCACAGCTTGGAGGCTTGAACAG (SEQ ID NO:51), CAGCTTGGAGGCTTGAA (SEQ ID NO:52), CTTGGAGGCTTGAA (SEQ ID NO:53), CTTGGAGGCTTGAACAG (SEQ ID NO:54), CAGCTTGGAGGCTT (SEQ ID NO:55), and GCACAGCTTGGAGGCTT (SEQ ID NO:56).

16. The method for the inhibiting the replication of hepatitis B virus (HBV) in an infected cell comprising administering to the cell an effective amount of a single stranded antisense oligonucleotide sufficient to bind to an mRNA derived from the HBV DNA genome and modulate an HBV-related function, wherein said oligonucleotide is selected from the group consisting of: CTTAGGACTACACTACAAGAG (SEQ ID NO:1), GACTACACTACAAGAG (SEQ ID NO:3), AGGACTACACTACAAGAGGTA (SEQ ID NO:4), TACACTACAAGAGGTA (SEQ ID NO:5), TCTTCCCCAGGATCCT (SEQ ID NO:6), GTACAAGTCGCGTCCCAGG (SEQ ID NO:9), CAAGAGGTACAAGTC (SEQ ID NO:12), CGACCACCTTTCTAAGACGGG (SEQ ID NO:13), CCTTTCTAAGACGGG (SEQ ID NO:14), CAAGACGGGGTA (SEQ ID NO:15), GACGGGGTACGACAT (SEQ ID NO:16), GTACGACATCTAGAA (SEQ ID NO:17), GTTTAAGAAATATTCCCAGCT (SEQ ID NO:31), GTTTAAGAAATATTC (SEQ ID NO:33), TCCCAGCTACAGGTA (SEQ ID NO:34), GAAATATTCCCAGCT (SEQ ID NO:35), and GAAATATTCCCAGCTACAGGTA (SEQ ID NO:38).

* * * * *

SEQUENCE LISTING (1) GENERAL INFORMATION:

(iii) NUMBER OF SEQUENCES: 56

(2) INFORMATION FOR SEQ ID NO: 1:

(i) SEQUENCE CHARACTERISTICS:
    (A) LENGTH: 21 base pairs
    (B) TYPE: nucleic acid
    (C) STRANDEDNESS: single (D) TOPOLOGY: linear (iv) ANTI-SENSE: YES (xi) SEQUENCE DESCRIPTION: SEQ ID NO: 1:

CTTAGGACTA CACTACAAGA G                                              21

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO: 2:

CTCTTGTAGT GTAGTCCTAA G                                              21

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 3:

GACTACACTA CAAGAG                                                    16

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 4:

AGGACTACAC TACAAGAGGT A                                              21

(2) INFORMATION FOR SEQ ID NO: 5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 5:

TACACTACAA GAGGTA                                                    16

(2) INFORMATION FOR SEQ ID NO: 6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 6:

TCTTCCCCAG GATCCT                                                16

(2) INFORMATION FOR SEQ ID NO: 7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 7:

TTTGGGGCGG ACATTG                                                16

(2) INFORMATION FOR SEQ ID NO: 8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 8:

CCTAAGAACA GTTGTT                                                16

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 9:

GTACAAGTCG CGTCCCAGG                                             19

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 10:

TAGGAGCTCT TCTAAC                                                16

(2) INFORMATION FOR SEQ ID NO: 11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 11:

TATTCCCTAG TCTTGT                                                16

(2) INFORMATION FOR SEQ ID NO: 12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 12:

CAAGAGGTAC AAGTC                                                  15

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 13:

CGACCACCTT TCTAAGACGG G                                      21

(2) INFORMATION FOR SEQ ID NO: 14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 14:

CCTTTCTAAG ACGGG                                                  15

(2) INFORMATION FOR SEQ ID NO: 15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 15:

TAAGACGGGG TA                                                        12

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 16:

GACGGGGTAC GACAT                                                  15

(2) INFORMATION FOR SEQ ID NO: 17:

(i) SEQUENCE CHARACTERISTICS:

```
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 17:

GTACGACATC TAGAA                                                      15

(2) INFORMATION FOR SEQ ID NO: 18:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO: 18:

CCCGTCTTAG AAAGGTGGTC G                                               21

(2) INFORMATION FOR SEQ ID NO: 19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 19:

ATCCGCTCCA CTTTTTCAAC                                                 20

(2) INFORMATION FOR SEQ ID NO: 20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO: 20:

GTTGAAAAAG TGGAGCGGAT                                                 20

(2) INFORMATION FOR SEQ ID NO: 21:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 21:

TCCACTTTTT CAAC                                                       14

(2) INFORMATION FOR SEQ ID NO: 22:

(i) SEQUENCE CHARACTERISTICS:
            (A) LENGTH: 15 base pairs
            (B) TYPE: nucleic acid
            (C) STRANDEDNESS: single
            (D) TOPOLOGY: linear
```

(iv) ANTI-SENSE: YES (xi) SEQUENCE DESCRIPTION: SEQ ID NO: 22:

CACTTTTTCA ACGTA                                                              15

(2) INFORMATION FOR SEQ ID NO: 23:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 23:

TTCAACGTAC CACGA                                                              15

(2) INFORMATION FOR SEQ ID NO: 24:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 24:

GTACCACGAC CACGC                                                              15

(2) INFORMATION FOR SEQ ID NO: 25:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 25:

CTTCACAACT ATCCTATCCC C                                                       21

(2) INFORMATION FOR SEQ ID NO: 26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO: 26:

GGGGATAGGA TAGTTGTGAA G                                                       21

(2) INFORMATION FOR SEQ ID NO: 27:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 27:

AACTATCCTA TCCCC                                                15

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 28:

TATCCTATCC CCGTA                                                15

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 29:

ATCCCCGTAA ACCAC                                                15

(2) INFORMATION FOR SEQ ID NO: 30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 30:

GTAAACCACC AGATA                                                15

(2) INFORMATION FOR SEQ ID NO: 31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 31:

GTTTAAGAAA TATTCCCAGC T                                         21

(2) INFORMATION FOR SEQ ID NO: 32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO: 32:

AGCTGGGAAT ATTTCTTAAA C                                         21

(2) INFORMATION FOR SEQ ID NO: 33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 33:

GTTTAAGAAA TATTC                                           15

(2) INFORMATION FOR SEQ ID NO: 34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 34:

TCCCAGCTAC AGGTA                                           15

(2) INFORMATION FOR SEQ ID NO: 35:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 35:

GAAATATTCC CAGCT                                           15

(2) INFORMATION FOR SEQ ID NO: 36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 36:

GGTTTAAGAA ATATT                                           15

(2) INFORMATION FOR SEQ ID NO: 37:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 37:

TCATCGAGGT TTAAG                                           15

(2) INFORMATION FOR SEQ ID NO: 38:

(i) SEQUENCE CHARACTERISTICS:
        (A) LENGTH: 22 base pairs (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 38:

GAAATATTCC CAGCTACAGG TA                    22

(2) INFORMATION FOR SEQ ID NO: 39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 39:

TTGAACAGTA GGTCATGAAC A                     21

(2) INFORMATION FOR SEQ ID NO: 40:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 40:

TTGAACAGTA GGACAT                           16

(2) INFORMATION FOR SEQ ID NO: 41:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 41:

CAGTAGGACA TGAACA                           16

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 42:

CAGTAGGACA TGAACAAGAG                       20

(2) INFORMATION FOR SEQ ID NO: 43:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 43:

TAGGACATGA ACAAGA                                                         16

(2) INFORMATION FOR SEQ ID NO: 44:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 44:

TAGGACATGA ACAAGAGATG A                                                   21

(2) INFORMATION FOR SEQ ID NO: 45:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 45:

AAAGCCACCC AAGGCACAGC T                                                   21

(2) INFORMATION FOR SEQ ID NO: 46:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 46:

CACCCAAGGC ACAGCT                                                         16

(2) INFORMATION FOR SEQ ID NO: 47:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 47:

ACCCCAAAGC CACCCAAGGC A                                                   21

(2) INFORMATION FOR SEQ ID NO: 48:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO: 48:

```
AAAGCCACCC AAGGCA                                                    16

(2) INFORMATION FOR SEQ ID NO: 49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 49:

ATGATCCCAA AGCCACCCAA G                                              21

(2) INFORMATION FOR SEQ ID NO: 50:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 50:

CCCAAAGCCA CCCAAG                                                    16

(2) INFORMATION FOR SEQ ID NO: 51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 51:

GCACAGCTTG GAGGCTTGAA CAG                                            23

(2) INFORMATION FOR SEQ ID NO: 52:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 52:

CAGCTTGGAG GCTTGAA                                                   17

(2) INFORMATION FOR SEQ ID NO: 53:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 53:

CTTGGAGGCT TGAA                                                      14

(2) INFORMATION FOR SEQ ID NO: 54:
```

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 54:

CTTGGAGGCT TGAACAG                                                 17

(2) INFORMATION FOR SEQ ID NO: 55:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 55:

CAGCTTGGAG GCTT                                                    14

(2) INFORMATION FOR SEQ ID NO: 56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO: 56:

GCACAGCTTG GAGGCTT                                                 17
```